(12) United States Patent
Coy

(10) Patent No.: US 9,220,760 B2
(45) Date of Patent: Dec. 29, 2015

(54) METHOD OF MODULATING THE PROLIFERATION OF MEDULLARY THYROID CARCINOMA CELLS

(75) Inventor: David H. Coy, New Orleans, LA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 606 days.

(21) Appl. No.: 11/799,594

(22) Filed: May 2, 2007

(65) Prior Publication Data

US 2007/0259811 A1    Nov. 8, 2007

Related U.S. Application Data

(63) Continuation of application No. 10/469,835, filed as application No. PCT/US02/06729 on Mar. 6, 2002, now abandoned.

(60) Provisional application No. 60/273,699, filed on Mar. 6, 2001.

(51) Int. Cl.
*C07K 14/655* (2006.01)
*A61K 38/31* (2006.01)
*A61K 38/08* (2006.01)

(52) U.S. Cl.
CPC ............. *A61K 38/31* (2013.01); *A61K 38/08* (2013.01)

(58) Field of Classification Search
None
See application file for complete search history.

(56) References Cited

U.S. PATENT DOCUMENTS

| | | | |
|---|---|---|---|
| 4,661,472 A * | 4/1987 | Rivier et al. | |
| 5,597,894 A | 1/1997 | Coy et al. | |
| 5,968,903 A | 10/1999 | Kaneko et al. | |
| 5,972,893 A | 10/1999 | Melmed et al. | |
| 6,180,082 B1 | 1/2001 | Woltering et al. | |

FOREIGN PATENT DOCUMENTS

| | | |
|---|---|---|
| WO | WO 95/04752 | 2/1995 |
| WO | WO 98/50063 | 11/1998 |
| WO | WO 99/26551 | 6/1999 |
| WO | WO 00/06185 | 2/2000 |
| WO | WO 01/00676 | 1/2001 |
| WO | WO 02/070555 A2 * | 9/2002 |

OTHER PUBLICATIONS

Hocart et al. (J. Med. Chem. 1999; 42: 1863-1871).*
Hocart et al. (J. Med. Chem. 1999; 42: 1863-1871, IDS).*
Dermer, G. B., "Another anniversary for the war on cancer," Bio/Technology, 1994, 12:320.
Freshney, R. I., "Culture of animal cells: A manual of basic technique," Alan R. Liss, Inc., 1983, New York, p. 4.
Gura, T., "Systems for identifying new drugs are often faulty," Science, 1997, 278:1041-1042.
Kebebew, E. et al., "Medullary Thyroid Cancer," Curr. Treatment Options in Oncology, 2000, 1:359-367.
Ahlman, H. et al., "The Relevance of Somatostatin Receptors in Thyroid Neoplasia," Yale J. of Biol. and Med., 1997, 70:523-533.
Ain, K. B. et al., "Somatostatin analogs affect proliferation o f human thyroid carcinoma cell lines in vitro", 1994, J. Clin. Endo. Metab., 78:1097-1102.
Ain, K. B. et al., "Somatostatin receptor subtype expression in human thyroid and thyroid carcinoma cell lines", J. Clin. Endo. and Metab., 1997, 82:1857-1862.
Baulieu, J. L. et al., "[$^{131}$I]-TYR3-Octreotide: Clinical dosimetry and use for internal radiotherapy of metastatic paraganglioma and carcinoid tumors", Nuc. Med. And Biolo., 2000, 27:809-813.
Berna, L. et al., "Use of Somatostatin Analogue Scintigraphy in the Localization of Recurrent Medullary Thyroid Carcinoma," Eu. J. of Nuclear Med., Nov. 1998, 25(11):1482-1488.
Buscail, L. et al., "Inhibition of cell proliferation by the somatostatin analogue RC-160 is mediated by somatostatin receptor subtypes SSTR2 and SSTR5 through different mechanisms", PNAS, 1995, 92:1580-1584.
Cattaneo, M. G. et al., "Selective stimulation of somatostatin receptor subtypes: differential effects on RAS/MAP kinase patheay and cell proliferation in human neuroblastoma cells", 2000, FEBS Letters, 481:271-276.
Forssell-Aronsson, E. B. et al., $^{111}$In-DPTA-D-Phe$^1$-Octreotide binding and somatostatin receptor subtypes in thyroid tumors, J. Nuc. Med., 2000, 41:636-642.
Frank-Raue, K. et al., "Therapy of metastatic medullary thyroid gland carcinoma with the somatostatin analog octreotide", Med. Klin., 1995, 90:63-66.
Gaztambide et al., "Short- and long-term effect of a long-acting somatostatin analogue, lanreotide (SR-L) on metastatic gastrinoma", 1999, *J. Endocrinol. Invest.*, 22: 144-146.
Gloge, A. et al., "The behavior of substrate analogues and secondary deuterium isotope effects in the phenylalanine ammonia-lyase reaction", 1988, Arch. Biochem Biophys., 359:1-7.
Hocart, S. J. et al., "Highly potent cyclic disulfide antagonists of somatostatin" J. Med. Chem., 1999, 42:1863-1871.
Kimura, N. et al., "Immunohistochemical Expression of Somatostatin Type 2A Receptor in Neuroendocrine Tumors," Clin. Cancer Res., Nov. 1999, 5:3483-3487.
Kolby, L. et al., "Somatostatin Receptor Subtypes, Octreotide Scintigraphy, and Clinical Response to Octreotide Treatment in Patients with Neuroendocrine Tumors," World. J. Surg., 1998, 22:679-683.
Mahler, C. et al., "Long-term treatment of metastatic medullary thyroid carcinoma with the somatostatin analogue octreotide", Clin. Endo., 1990, 33:261-269.
Mato, E. et al., "Somatostatin and Somatostatin Receptor Subtype Gene Expression in Medullary Thyroid Carcinoma," J. Clin. Endocrinology and Metabolism, 1998, 83(7):2417-2420.

(Continued)

*Primary Examiner* — Misook Yu
*Assistant Examiner* — Nelson B Moseley, II
(74) *Attorney, Agent, or Firm* — Janice M. Klunder; Ipsen Bioscience, Inc.

(57) ABSTRACT

The present invention is directed to a method of decreasing the rate of proliferation of medullary thyroid carcinoma cells which comprises contacting medullary thyroid carcinoma cells with one or more SSTR2 agonist. A somatostatin receptor antagonist having the formula Cpa-cyclo(D-Cys-4-Pal-D-Trp-Lys-Thr-Cys)-Nal-NH$_2$ is also disclosed.

1 Claim, 7 Drawing Sheets

(56) References Cited

OTHER PUBLICATIONS

Mottet et al., "Hemodynamic effects of the somatostatin analog lanreotide in humans: placebo-controlled, cross-over dose-ranging echo-doppler study", 1998, Hepatology, 27:920-925.

Reubi, J. C. et al., "Expression and Localization of Somatostatin Receptor SSTR1, SSTR2, and SSTR3 Messenger RNAs in Primary Human Tumors using in situ Hybridization," Cancer Research, 1994, 54:3455-3459.

Saveanu, A. et al., "BIM-23244, a somatostatin receptor subtype 2- and 5- selective analog with enhanced efficacy in suppressing growth hormone (GH) from octreotide-resistant human GH-secreting ademonas", J. Clin. Endocrinology and Metabolism, 2001, 86:140-145.

Shimon, I. et al., "Somatostatin receptor (SSTR) subtype-selective analogues differentially suppress in vitro growth hormone and prolactic in human pituitary adenomas," J. Clin. Invest., 100(9):2386-2392, 1997.

Smith-Jones, P. M. et al., "DOTA-Lanreotide: A novel somatostatin analog for tumor diagnosis and therapy", Endocrinology, 1999, 140:5136-5148.

Tomassetti, P. et al., "Slow-release lanreotide treatment in endocrine gastrointestinal tumors", Am. J. Gastroenterology, 1998, 93:1468-1471.

Virgolini, I. et al., "In vitro and in vivo studies of three radiolabelled somatostatin analogues: 123I-Octreotide (OCT), 123I-Tyr-3-OCT and 111In-DPTA-D-Phe-1-OCT", European J. Nuc. Med., 1996, 23:1388-1399.

Vitale, G. et al., "Slow release lanreotide in combination with interferon-a2b in the treatment of symptomatic advanced medullary thyroid carcinoma", J. Clin. Endo. and Metab., 2000, 85:983-988.

Woltering, E. A., et al., "Synthesis and characterization of multiply-tyrosinated, multiply-iodinated somatostatin analogs", J. Pep. Res., 1999, 53:201-213.

Folkers, K. et al., "Antagonists of the luteinizing hormone releasing hormone with pyridyl-alanines which completely inhibit ovulation at nanogram dosage", Biochem. Biophys. Res. Com., 1983, 11:1089-1095.

Shimeno H. et al., "Effects of pyridylalanine analogs, glycyrrhizin and cortisone on brain biogenic amine contents, tryptophan pyrrolase and tyrosine aminotransferase in rats", Yakugaku Zasshi, 1980, 100:p. 1078 and p. 1084.

* cited by examiner

SEQUENCE LISTING

<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is D-Phe
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MOD_RES
<222> LOCATION: (8)..(8)
<223> OTHER INFORMATION: AMIDATION

<400> SEQUENCE: 1

Xaa Phe Trp Xaa Lys Thr Phe Thr
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is D-Nal (D-naphthyl alanine)
<220> FEATURE:
<221> NAME/KEY: DISULFID
<222> LOCATION: (2)..(7)
<223> OTHER INFORMATION: cyclic peptide
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MOD_RES
<222> LOCATION: (8)..(8)
<223> OTHER INFORMATION: AMIDATION

<400> SEQUENCE: 2

Xaa Cys Tyr Xaa Lys Val Cys Thr
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is a non-naturally occurring amino
      acid, Tic (1,2,3,4-tetrahydroisoquinoline-3-carboxylic acid)
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MISC_FEATURE
<222> LOCATION: (3)..(3)
<223> OTHER INFORMATION: residue is D-Trp
<220> FEATURE:
<221> NAME/KEY: MISC_FEATURE
<222> LOCATION: (5)..(5)

```
<223> OTHER INFORMATION: residue is Abu (2-aminobutyric acid)

<400> SEQUENCE: 3

Xaa Tyr Xaa Lys Xaa Phe
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is D-Phe
<220> FEATURE:
<221> NAME/KEY: MOD_RES
<222> LOCATION: (1)..(1)
<223> OTHER INFORMATION: modification: 4-(2-Hydroxyethyl)-1-
      piperazinylacetyl-
<220> FEATURE:
<221> NAME/KEY: DISULFID
<222> LOCATION: (2)..(7)
<223> OTHER INFORMATION: cyclic peptide
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MISC_FEATURE
<222> LOCATION: (6)..(6)
<223> OTHER INFORMATION: residue is Abu (2-aminobutyric acid)
<220> FEATURE:
<221> NAME/KEY: MOD_RES
<222> LOCATION: (8)..(8)
<223> OTHER INFORMATION: AMIDATION

<400> SEQUENCE: 4

Xaa Cys Tyr Xaa Lys Xaa Cys Thr
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-(2-Hydroxyethyl)-1-piperazine-2-
      ethanesulfonyl
<220> FEATURE:
<221> NAME/KEY: MISC_FEATURE
<222> LOCATION: (1)..(1)
<223> OTHER INFORMATION: residue is D-Phe
<220> FEATURE:
<221> NAME/KEY: DISULFID
<222> LOCATION: (2)..(7)
<223> OTHER INFORMATION: cyclic peptide
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MISC_FEATURE
<222> LOCATION: (6)..(6)
<223> OTHER INFORMATION: residue is Abu (2-aminobutyric acid)
<220> FEATURE:
<221> NAME/KEY: MOD_RES
<222> LOCATION: (8)..(8)
<223> OTHER INFORMATION: AMIDATION

<400> SEQUENCE: 5
```

```
Xaa Cys Tyr Xaa Lys Xaa Cys Thr
1               5
```

<210> SEQ ID NO 6
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is p-Cl-Phe
<220> FEATURE:
<221> NAME/KEY: DISULFID
<222> LOCATION: (2)..(7)
<223> OTHER INFORMATION: cyclic peptide
<220> FEATURE:
<221> NAME/KEY: MISC_FEATURE
<222> LOCATION: (2)..(2)
<223> OTHER INFORMATION: residue is D-Cys
<220> FEATURE:
<221> NAME/KEY: MISC_FEATURE
<222> LOCATION: (3)..(3)
<223> OTHER INFORMATION: residue is L-3-(Pyrid-4-yl)alanyl
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MISC_FEATURE
<222> LOCATION: (8)..(8)
<223> OTHER INFORMATION: residue is Nal (2-napthyl alaline)
<220> FEATURE:
<221> NAME/KEY: MOD_RES
<222> LOCATION: (8)..(8)
<223> OTHER INFORMATION: AMIDATION

<400> SEQUENCE: 6

```
Xaa Xaa Xaa Xaa Lys Thr Cys Xaa
1               5
```

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
agccggttga ctattacgcc                                               20

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
gctctcactt ctaccattgt c                                             21

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
ggtgaagtcc tctggaatcc                                              20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
ccattgccag tagacagagc                                              20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
tcatctgcct ctgctacctg                                              20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
gagcccaaag aaggcaggct                                              20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 13
cggcagtctt cgtggtctac                                              20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 14
gcatcaaggt cggtcacgac                                              20

<210> SEQ ID NO 15
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 15
aacacgctgg tcatctacgt ggt                                          23

<210> SEQ ID NO 16
<211> LENGTH: 22
<212> TYPE: DNA
<213> ORGANISM: Artificial Sequence

```
<220> FEATURE:
<223> OTHER INFORMATION: oligonucleotide primer

<400> SEQUENCE: 16
agacactggt gaactggttg ac                                          22

<210> SEQ ID NO 17
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 17
atgacccctt cattgacctc                                             20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
aagtggtcgt tgagggcaat                                             20

<210> SEQ ID NO 19
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: residue is D-Phe
<220> FEATURE:
<221> NAME/KEY: MISC_FEATURE
<222> LOCATION: (4)..(4)
<223> OTHER INFORMATION: residue is D-Trp
<220> FEATURE:
<221> NAME/KEY: MOD_RES
<222> LOCATION: (8)..(8)
<223> OTHER INFORMATION: AMIDATION

<400> SEQUENCE: 19

Xaa Phe Phe Xaa Lys Thr Phe Thr
1               5
```

METHOD OF MODULATING THE PROLIFERATION OF MEDULLARY THYROID CARCINOMA CELLS

This application is a continuation application of U.S. Ser. No. 10/469,835, filed Apr. 20, 2004 now abandoned, which is a United States national filing under 35 U.S.C. §371 of international (PCT) application No. PCT/US02/06729, filed Mar. 6, 2002, designating the United States, and claiming priority to U.S. provisional application Ser. No. 60/273,699, filed Mar. 6, 2001.

BACKGROUND OF THE INVENTION

Somatostatin (SS), a tetradecapeptide discovered by Brazeau et al., has been shown to have potent inhibitory effects on various secretory processes in tissues such as pituitary, pancreas and gastrointestinal tract. SS also acts as a neuromodulator in the central nervous system. These biological effects of SS, all inhibitory in nature, are elicited through a series of G protein coupled receptors, of which five different subtypes have been characterized (SSTR1-SSTR5) (Reubi J C, et al., Cancer Res 47: 551-558, Reisine T, et al., Endocrine Review 16: 427-442, Lamberts S W, et al., Endocr Rev 12: 450-482, 4 Patel Y C, 1999 Front Neuroendocrinology 20: 157-198). These five subtypes have similar affinities for the endogenous SS ligands but have differing distribution in various tissues. Somatostatin binds to the five distinct receptor (SSTR) subtypes with relatively high and equal affinity for each subtype.

There is evidence that SS regulates cell proliferation by arresting cell growth via SSTR1, 2, 4, and 5 subtypes (Buscail L, et al., 1995 Proc Natl Acad Sci USA 92: 1580-1584; Buscail L, et al., 1994 Proc Natl Acad Sci USA 91: 2315-2319; Florio T, et al., 1999 Mol Endocrinol 13: 24-37; Sharma K, et al., 1999 Mol Endocrinol 13: 82-90), or by inducing apoptosis via SSTR3 subtype (Sharma K, et al., 1996 Mol Endocrinol 10: 1688-1696). SS and various analogues have been shown to inhibit normal and neoplastic cell proliferation in vitro and vivo (Lamberts S W, et al., Endocr Rev 12: 450-482) via specific SS receptors (SSTR's) (Patel Y C, 1999 Front Neuroendocrinology 20: 157-198) and possibly different postreceptor actions (Weckbecker G, et al., Pharmacol Ther 60: 245-264; Bell G I, Reisine T 1993 Trends Neurosci 16: 34-38; Patel Y C, et al., Biochem Biophys Res Commun 198: 605-612; Law S F, et al., Cell Signal 7:1-8). In addition, there is evidence that distinct SSTR subtypes are expressed in normal and neoplastic human tissues (Virgolini I, et al., Eur J Clin Invest 27: 645-647), conferring different tissue affinities for various SS analogues and variable clinical response to their therapeutic effects.

Binding to the different types of somatostatin receptor subtypes has been associated with the treatment of various conditions and/or diseases. For example, the inhibition of growth hormone has been attributed to the somatostatin type-2 receptor ("SSTR2") (Raynor, et al., Molecular Pharmacol. 43:838 (1993); Lloyd, et al., Am. J. Physiol. 268:G102 (1995)) while the inhibition of insulin has been attributed to the somatostatin type-5 receptor ("SSTR5") (Coy, et al. 197: 366-371 (1993)). Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin receptor subtypes include inhibition of insulin and/or glucagon for treating diabetes mellitus, angiopathy, proliferative retinopathy, dawn phenomenon and nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis; treatment of inflammatory disorders such as arthritis; retinopathy; chronic allograft rejection; angioplasty; preventing graft vessel and gastrointestinal bleeding. It is preferred to have an analog which is selective for the specific somatostatin receptor subtype or subtypes responsible for the desired biological response, thus, reducing interaction with other receptor subtypes which could lead to undesirable side effects.

Somatostatin (SS) and its receptors (SSTR1 to SSTR5) are expressed in normal human parafollicular C cells and medullary thyroid carcinoma (MTC) cells. MTC is a tumor originating from thyroid parafollicular C cells that produces calcitonin (CT), somatostatin, as well as several other peptides (Moreau J P, et al., Metabolism 45 (8 Suppl 1): 24-26). Recently, Mato et al. showed that SS and SSTR's are expressed in human MTC (Mato E, et al., J Clin Endocrinol Metab 83: 2417-2420). It has been documented that SS and its analogues induce a decrease in plasma CT levels and a symptomatic improvement in MTC patients. However, until now the antiproliferative activity of SS analogues on tumor cells had not been clearly demonstrated (Mahler C, et al., Clin Endocrinol 33: 261-9; Lupoli G, et al., Cancer 78: 1114-8; Smid W M, et al., Neth J Med 40: 240-243). Thus, development and assessment of SSTR subtype analogues selective on MTC cell growth provides a useful tool for clinical application. Until now, no data concerning specific SSTR subtype involvement in MTC cell growth regulation have been reported.

The present invention relates to the discovery that the human MTC cell line TT, which displays MTC cell characteristics (Zabel M, et al., 1992 Histochemistry 102: 323-327, 2 Gagel R F, et al., 1986 Endocrinology 118: 1643-1651, Liu J L, et al., 1995 Endocrinology 136: 2389-2396) and which stably expresses all the SSTR subtypes, responds to SSTR2 and SSTR5 activation by subtype selective agonists with two different patterns in terms of [$^3$H]thy incorporation and cell number. SSTR2 preferential agonists significantly suppress [$^3$H]thy incorporation, i.e., inhibit DNA synthesis, and reduce cell proliferation. SSTR5 selective agonists significantly increase [$^3$H]thy incorporation in TT cells, i.e., increase DNA synthesis, but alone fail to influence cell proliferation. Further, SSTR2 antagonists counteract the action of SSTR2 preferential agonists on TT cells. Further still, increasing concentrations of an SSTR5 selective agonist dose-dependently prevents the suppression of TT cell [$^3$H]thy incorporation and proliferation produced by an SSTR2 preferential agonist, and vice versa, showing an antagonism between such agonists.

Hetero- and homodimeric interactions between subtypes of the opiate (Jordan B A, et al., 1999 Nature 399:697-700.) and SS (Rocheville M, et al., 2000 J. Biol. Chem. 275:7862-7869) receptor families have been recently demonstrated. Studies in cultured pituitary adenoma cells have demonstrated that SSTR subtype 2 and 5 act synergistically in the suppression of growth hormone and prolactin secretion (Shimon I, et al., 1997 J. Clinical Invest. 100:2386-2392, Jaquet P, et al., 2000 J Clin Endocrinol Metab. 85:781-792). The finding that SSTR5 activation reduces the antiproliferative activity mediated by SSTR2 differs from results in other tissues (Patel Y C, 1999 Front Neuroendocrinology 20: 157-198, Buscail L, et al., 1995 Proc Natl Acad Sci USA 92: 1580-

1584, Buscail L, et al., 1994 Proc Natl Acad Sci USA 91: 2315-2319, Sharma K, et al., 1996 Mol Endocrinol 10: 1688-1696). This is the first demonstration that SSTR subtypes 2 and 5 can act antagonistically in regulating cell growth.

Thus, SSTR2 and SSTR5 preferential agonists exert differential effects on proliferation of human medullary thyroid TT cell line in vitro, according to their specific SSTR selectivity. Proliferation of the TT cell line can be reduced by SSTR2 selective agonists, but not by SSTR5 agonists, and an SSTR5 agonist can prevent SSTR2 mediated antiproliferative effects. The key inhibitory role of SSTR2 on MTC cell proliferation demonstrates that analogues with enhanced SSTR2 affinity and selectivity versus SSTR5 would be useful as antiproliferative agents in MTC treatment.

SUMMARY OF THE INVENTION

The present invention is based on the discovery that somatostatin agonists selective for SSTR-2 are effective in reducing the rate of proliferation of medullary thyroid carcinoma cells, and that somatostatin agonists selective for SSTR-5 are effective in attenuating this SSTR-2 agonist-induced reduction in rate of proliferation.

In one aspect, the present invention is directed to a method of modulating the rate of proliferation of MTC cells which comprises contacting MTC cells with one or more SSTR2 agonist and one or more SSTR5 agonist, wherein said SSTR2 agonist serves to reduce the rate of proliferation of the MTC cells and said SSTR5 agonist serves to attenuate the SSTR-2 agonist-induced reduction in proliferation rate.

In one embodiment, the invention is directed to the immediately foregoing method wherein said SSTR-5 agonist is D-Phe-Phe-Trp-D-Trp-Lys-Thr-Phe-Thr-NH$_2$ (SEQ ID NO: 1) or a pharmaceutically acceptable salt thereof.

In another embodiment the invention is directed to a method of decreasing the rate of proliferation of medullary thyroid carcinoma cells which comprises contacting medullary thyroid carcinoma cells with one or more SSTR2 agonist or a pharmaceutically acceptable salt thereof.

In a preferred example of the immediately foregoing embodiment the SSTR-2 agonist is a SSTR-2 selective agonist. In a more preferred example, the SSTR-2 agonist or pharmaceutically acceptable salt thereof has a Ki value for SSTR-5 that is at least 2 times higher than it has for SSTR-2, more preferably at least 5 times higher than it has for SSTR-2, more preferably still at least 10 times higher than it has for SSTR-2.

In another preferred example of the foregoing embodiment the SSTR-2 agonist or pharmaceutically acceptable salt thereof has a Ki value of less than 5 nM, more preferably less than 1 nM.

In another preferred example of the foregoing embodiment, the SSTR-2 selective agonist is a compound selected from the list consisting of D-Nal-cyclo[Cys-Tyr-D-Trp-Lys-Val-Cys]-Thr-NH$_2$ (SEQ ID NO: 2), cyclo[Tic-Tyr-D-Trp-Lys-Abu-Phe] (SEQ ID NO: 3), 4-(2-Hydroxyethyl)-1-piperazinylacetyl-D-Phe-cyclo(Cys-Tyr-D-Trp-Lys-Abu-Cys)-Thr-NH$_2$ (SEQ ID NO: 4), and 4-(2-Hydroxyethyl)-1-piperazine-2-ethanesulfonyl-D-Phe-cyclo(Cys-Tyr-D-Trp-Lys-Abu-Cys)-Thr-NH$_2$ (SEQ ID NO: 5); or a pharmaceutically acceptable salt thereof, wherein "4-(2-Hydroxyethyl)-1-piperazinylacetyl" denotes the structure:

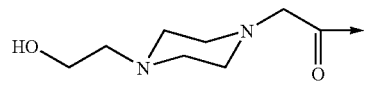

and "4-(2-Hydroxyethyl)-1-piperazine-2-ethanesulfonyl-" denotes the structure:

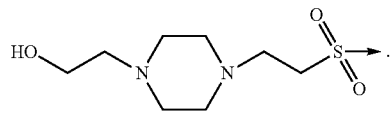

In a third embodiment, the invention is directed to a method of treating medullary thyroid carcinoma which comprises administering to a patient in need thereof an effective amount of a SSTR2 agonist.

In a preferred example of the third embodiment the SSTR-2 agonist is a SSTR-2 selective agonist. In a more preferred example, the SSTR-2 agonist or pharmaceutically acceptable salt thereof has a Ki value for SSTR-5 that is at least 2 times higher than it has for SSTR-2, more preferably at least 5 times higher than it has for SSTR-2, more preferably still at least 10 times higher than it has for SSTR-2.

In another preferred example of the third embodiment the SSTR-2 agonist or pharmaceutically acceptable salt thereof has a Ki value of less than 5 nM, more preferably less than 1 nM.

In yet another preferred example of the third embodiment, the SSTR-2 selective agonist is a compound selected from the list consisting of D-Nal-cyclo[Cys-Tyr-D-Trp-Lys-Val-Cys]-Thr-NH$_2$ (SEQ ID NO: 2), cyclo[Tic-Tyr-D-Trp-Lys-Abu-Phe] (SEQ ID NO: 3), 4-(2-Hydroxyethyl)-1-piperazinylacetyl-D-Phe-cyclo(Cys-Tyr-D-Trp-Lys-Abu-Cys)-Thr-NH$_2$ (SEQ ID NO: 4), and 4-(2-Hydroxyethyl)-1-piperazine-2-ethanesulfonyl-D-Phe-cyclo(Cys-Tyr-D-Trp-Lys-Abu-Cys)-Thr-NH$_2$ (SEQ ID NO: 5); or a pharmaceutically acceptable salt thereof, wherein "4-(2-Hydroxyethyl)-1-piperazinylacetyl" and "4-(2-Hydroxyethyl)-1-piperazine-2-ethanesulfonyl-" are as previously defined.

Importantly, as is well known in the art, standard radioactive iodine therapy, e.g., administration of a radioactive iodine salt to a patient, is not available for the treatment of medullary thyroid carcinoma since parafollicular cells do not take up iodine. Thus in another aspect the invention provides a method of treating medullary thyroid carcinoma patient comprising administering to a patient in need thereof an effective amount of a SSTR2 agonist or a pharmaceutically acceptable salt thereof, wherein said SSTR-2 agonist or pharmaceutically acceptable salt thereof comprises a Tyr(I) residue, wherein the iodine atom of said Tyr(I) residue comprises a radioactive iodine isotope. Preferably said iodine isotope comprises $^{125}$I, $^{127}$I or $^{131}$I.

In one embodiment of said medullary thyroid carcinoma cells have formed metastases outside the thyroid. In a further embodiment said metastases are present in the lymph, the lung, the liver, the brain, or in bone.

CHO-K1 cells, expressing the human SSTR2, were harvested as described in Material and Methods and then the SS analogues ($10^{-7}$-$10^{-6}$ M) were added for measurement of intracellular $Ca^{2+}$ mobilization, expressed as the ratio between the intracellular calcium concentration measured after the addition of SS analogues and the value observed at basal level. The excitation and emission wavelengths were 340 and 510 nm, respectively. The data are represented as mean±SEM.

Figure 2:
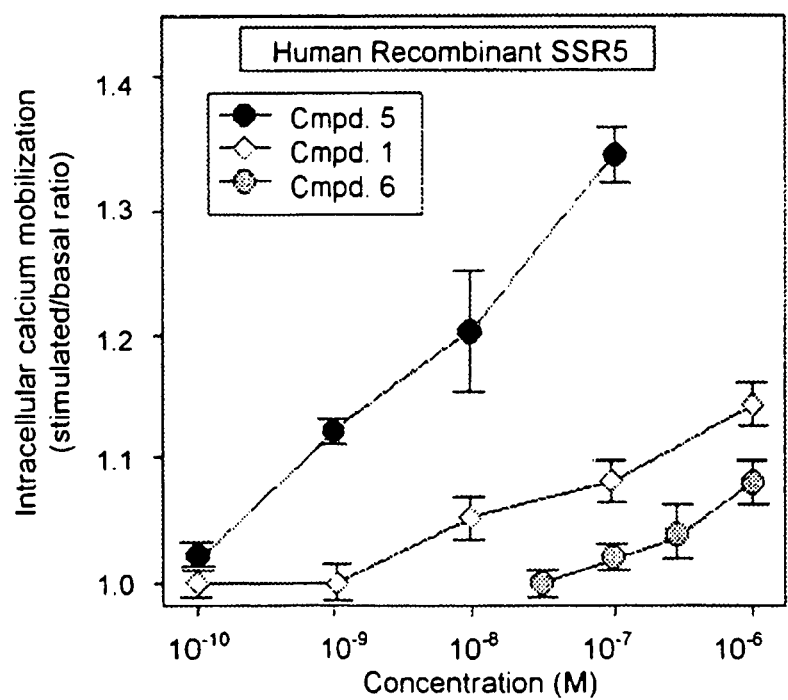

FIG. 2: In Vitro SSTR5 Mediated Intracellular Calcium Mobilization

CHO-K1 cells, expressing the human SSTR5, were harvested as described in Material and Methods and then the SS analogues ($10^{-7}$-$10^{-6}$ M) were added for measurement of intracellular $Ca^{2+}$ mobilization, expressed as the ratio between the intracellular calcium concentration measured after the addition of SS analogues (Compound 1, Compound 5 and Compound 6) and the value observed at basal level. The excitation and emission wavelengths were 340 and 510 nm, respectively. The data are represented as mean±SEM.

The structures of the compounds appearing in FIG. 2 are as follows:

Compound 1: D-Nal-cyclo[Cys-Tyr-D-Trp-Lys-Val-Cys]-Thr-$NH_2$ (SEQ ID NO: 2);
Compound 2: cyclo[Tic-Tyr-D-Trp-Lys-Abu-Phe] (SEQ ID NO: 3);
Compound 3: 4-(2-Hydroxyethyl)-1-piperazinylacetyl-D-Phe-cyclo(Cys-Tyr-D-Trp-Lys-Abu-Cys)-Thr-$NH_2$ (SEQ ID NO: 4);
Compound 4: 4-(2-Hydroxyethyl)-1-piperazine-2-ethanesulfonyl-D-Phe-cyclo(Cys-Tyr-D-Trp-Lys-Abu-Cys)-Thr-$NH_2$ (SEQ ID NO: 5);
Compound 5: D-Phe-Phe-Trp-D-Trp-Lys-Thr-Phe-Thr-$NH_2$ (SEQ ID NO: 1); and
Compound 6: Cpa-cyclo(D-Cys-4-Pal-D-Trp-Lys-Thr-Cys)-Nal-$NH_2$ (SEQ ID NO: 6).

Figure 3:
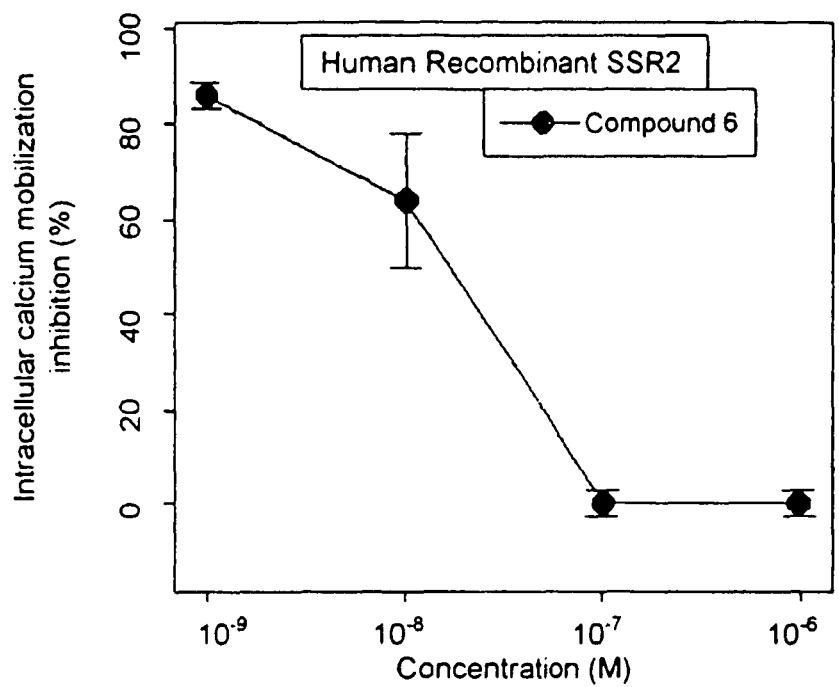

FIG. 3: In Vitro Inhibition of SS-Stimulated Intracellular Calcium Mobilization by SSTR2 Antagonist CHO-K1 cells, expressing the human SSTR2, were harvested as described in Material and Methods, and then Compound 6 ($10^{-9}$-$10^{-6}$ M) and SS (10 nM) were added for measurement of the effect of Compound 6 on SS ($10^{-8}$ M)-stimulated intracellular calcium mobilization, and expressed as the percentage vs. SS alone. The excitation and emission wavelengths were 340 and 510 nm, respectively. The data are represented as mean±SEM.

Figure 4:
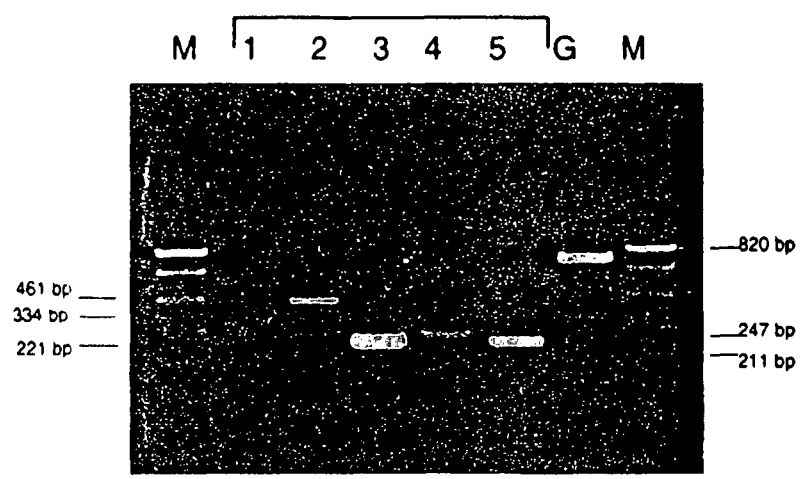

FIG. 4: Somatostatin Receptors mRNA Expression in TT Cells.

Extracted RNA (1 µg/reaction) was treated with deoxyribonuclease and subjected to reverse transcription using Oligo (dT) as primer. Samples incubated without RT enzyme served as control. Aliquots from the generated cDNA and the negative controls were subjected to subsequent PCR amplification of SSTR's, using the primers indicated in Table 1. PCR products were resolved on a 2% agarose gel. The expected PCR products of SSTR 1-5 are depicted in A (lane M, PCR Marker; G, PCR product of GAPDH amplification).

Figure 5:
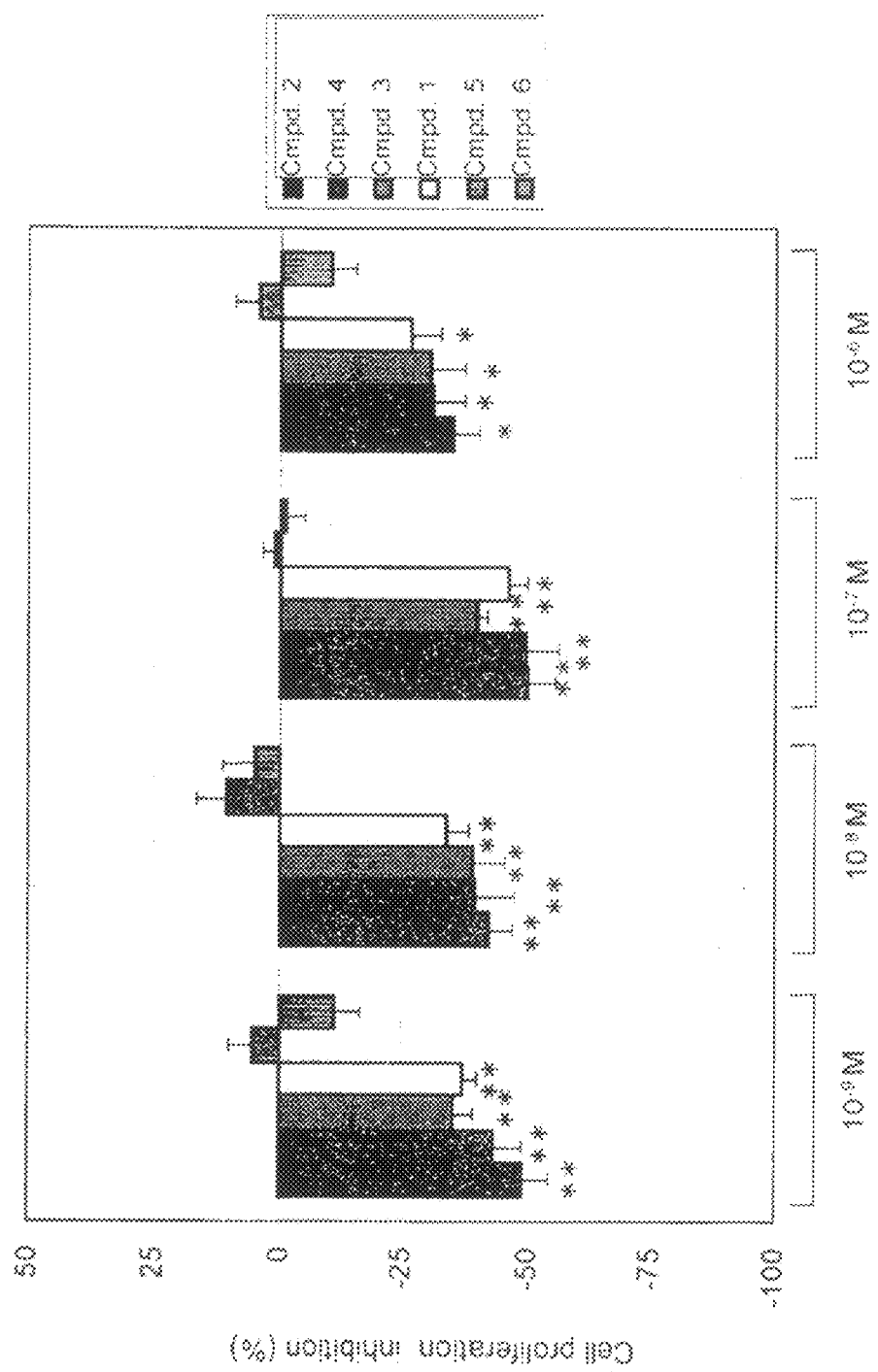

FIG. 5: Effect of SS Analogues on [$^3$H]thy Incorporation in TT Cells.

Cells were incubated in 24-well plates for 48 hours in a culture medium supplemented with SS analogues at various concentrations ($10^{-9}$, $10^{-8}$, $10^{-7}$, and $10^{-6}$ M). Control wells were treated with vehicle solution and [$^3$H]thy incorporation was measured as radioactivity in TCA-precipitated material. Data from six individual experiments evaluated independently in quadruplicate are expressed as the mean±SEM percent [$^3$H]thy incorporation inhibition versus untreated control cells *$P<0.05$ and **$P<0.01$ vs. control.

Figure 6:
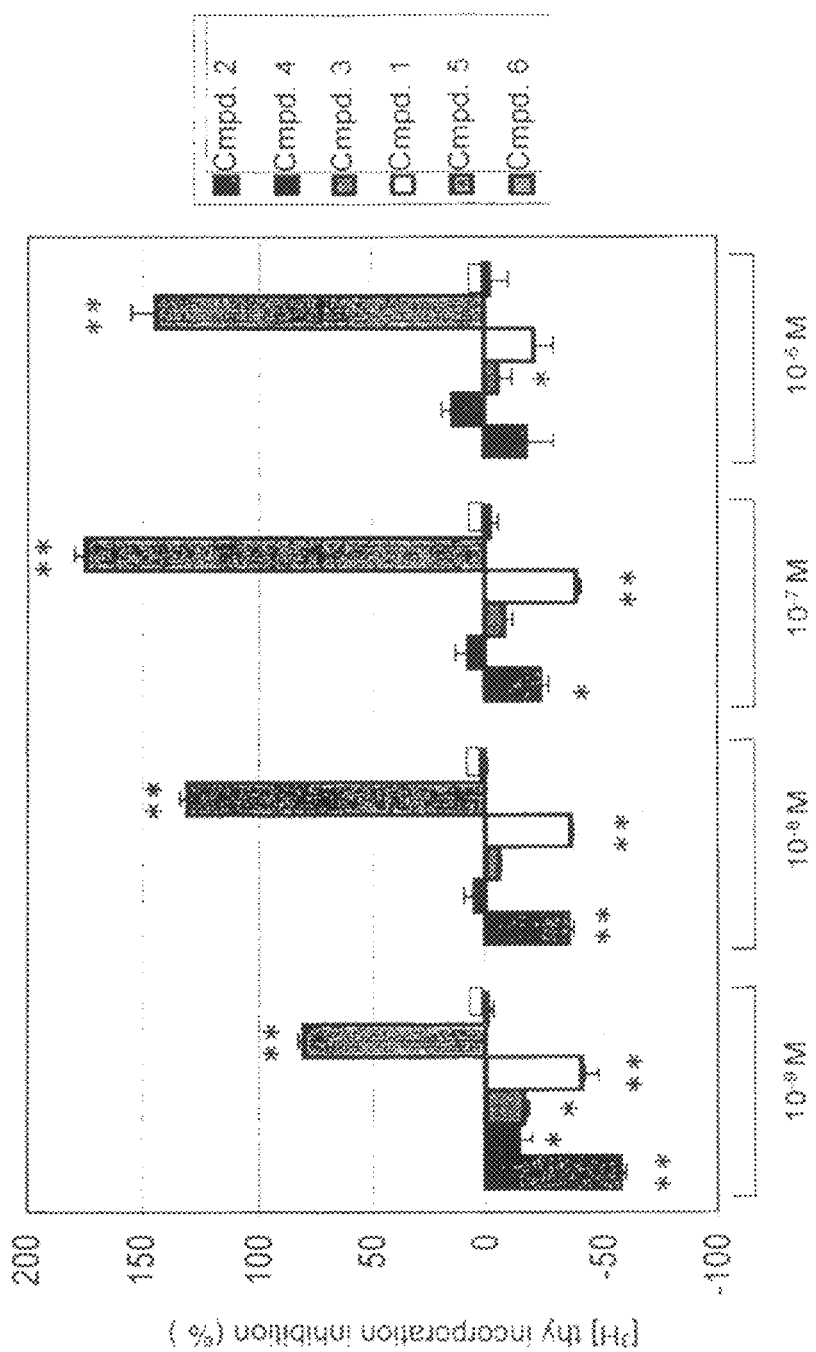

FIG. 6: Effect of SS Analogues on TT Cells Proliferation.

Cells were incubated in 96-well plates for 48 hours in a culture medium supplemented with SS analogues at various concentrations ($10^{-9}$, $10^{-8}$, $10^{-7}$, and $10^{-6}$ M). Control wells were treated with vehicle solution. TT cell proliferation was measured as absorbance at 490 nM of each well. Data from six individual experiments were evaluated independently with eight replicates expressed as the mean±SEM percent cell proliferation inhibition versus untreated control cells *$P<0.05$ and **$P<0.01$ vs. control.

Figure 7:
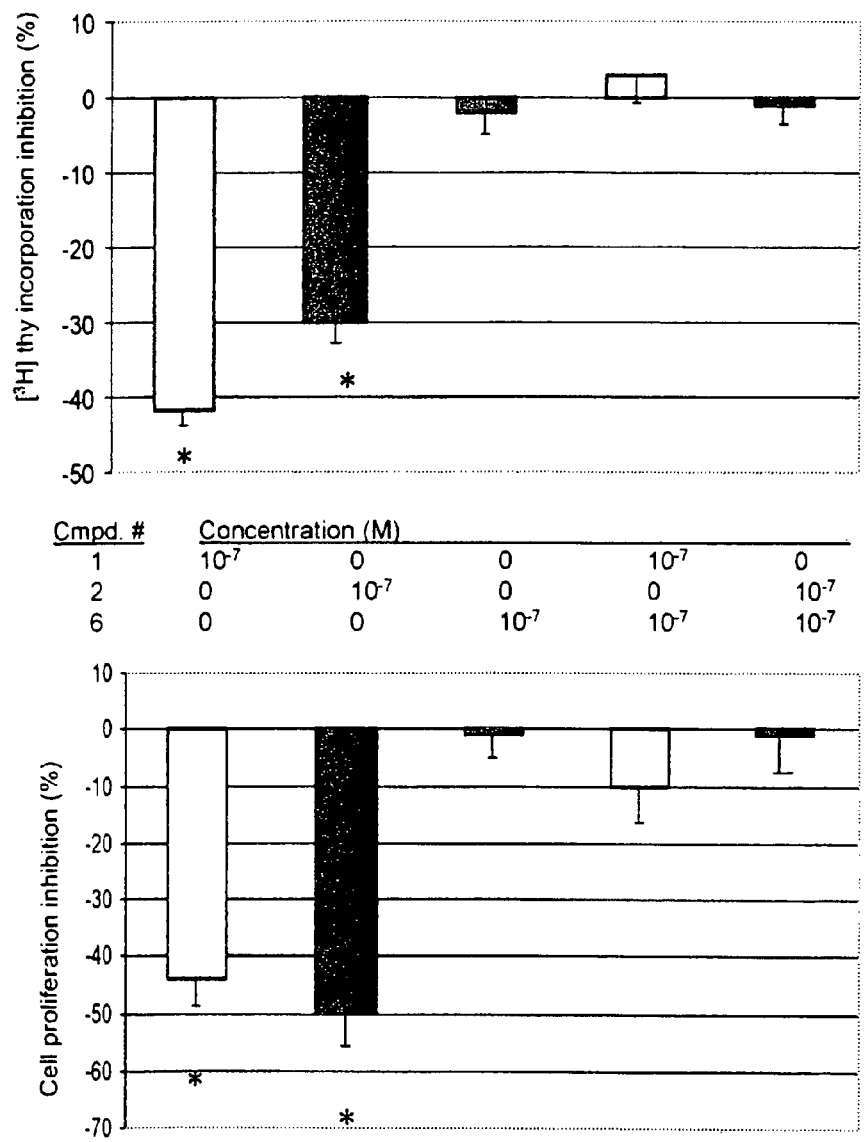

FIG. 7: Effect of SSTR2 Selective Antagonist on TT Cell [$^3$H]thy Incorporation and Cell Proliferation During Treatment with SSTR2 Agonist.

Upper panel: Cells were incubated in 24-well plates for 48 hours in a culture medium supplemented with 100 nM Compound 1 or Compound 2, with or without Compound 6 ($10^{-7}$ M). Control wells were treated with vehicle solution. [$^3$H]thy incorporation was measured as radioactivity in TCA-precipitated material. Data from six individual experiments were evaluated independently with four replicates expressed as the mean±SEM percent [$^3$H]thy incorporation inhibition versus untreated control cells *$P<0.05$ and **$P<0.01$ vs. control.

Lower panel: Cells were incubated in 96-well plates for 48 hours in a culture medium supplemented with $10^{-7}$ M Compound 1 or Compound 2, with or without Compound 6 ($10^{-7}$ M). Control wells were treated with vehicle solution. TT cell proliferation was measured as absorbance at 490 nM of each well. Data from six individual experiments were evaluated independently with eight replicates expressed as the mean±SEM percent cell proliferation inhibition versus untreated control cells *$P<0.05$ and **$P<0.01$ vs. control.

Figure 8:
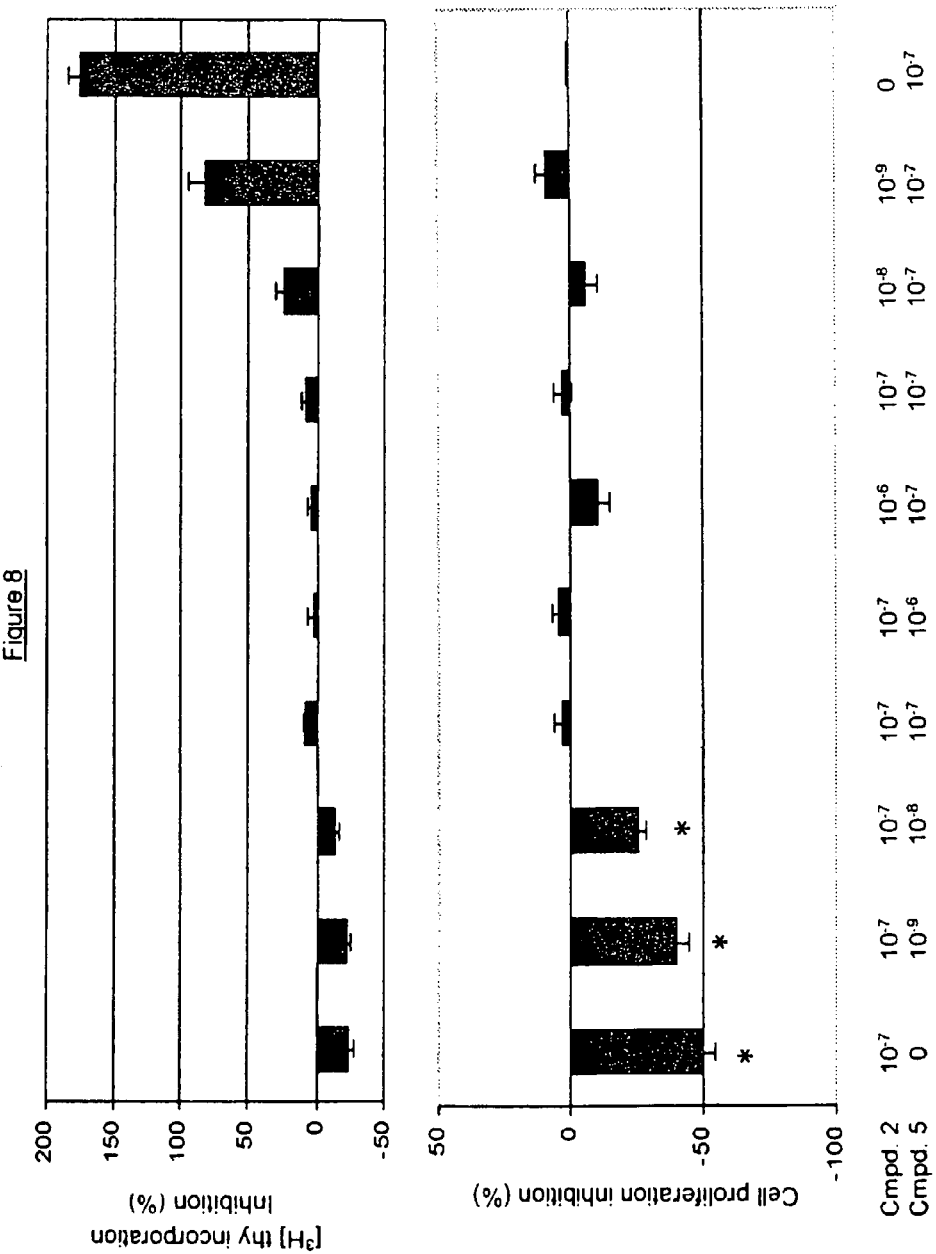

FIG. 8: Effect of SSTR5 Selective Agonist on TT Cell [$^3$H]thy Incorporation and Cell Proliferation During Treatment with SSTR2 Selective Agonist.

Upper panel: Cells were incubated in 24-well plates for 48 hours in a culture medium supplemented with Compound 2 ($10^{-7}$ M) without or with increasing concentrations of Compound 5 ($10^{-9}$, $10^{-8}$, $10^{-7}$, and $10^{-6}$ M), or with Compound 5 ($10^{-7}$ M) with or without decreasing concentrations of Compound 2 ($10^{-6}$, $10^{-7}$, $10^{-8}$, and $10^{-9}$ M). Control wells were treated with vehicle solution. [$^3$H]thy incorporation was measured as radioactivity in TCA-precipitated material. Data from six individual experiments were evaluated independently with four replicates expressed as the mean±SEM percent [$^3$H]thy incorporation inhibition versus untreated control cells *$P<0.05$ and **$P<0.01$ vs. control.

Lower panel: Cells were incubated in 96-well plates for 48 hours in a culture medium supplemented with Compound 2 ($10^{-7}$ M) without or with increasing concentrations of Compound 5 ($10^{-9}$, $10^{-8}$, $10^{-7}$, and $10^{-6}$ M), or with Compound 5 ($10^{-7}$ M) with or without decreasing concentrations of Compound 2 ($10^{-6}$, $10^{-7}$, $10^{-8}$, and $10^{-9}$ M). Control wells were treated with vehicle solution and TT cell proliferation was measured as absorbance at 490 nM of each well. Data from six individual experiments were evaluated independently with eight replicates expressed as the mean±SEM percent cell proliferation inhibition versus untreated control cells *$P<0.05$ and **$P<0.01$ vs. control.

DETAILED DESCRIPTION OF THE INVENTION

It is believed that one skilled in the art can, based on the description herein, utilise the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference, each in its entirety.

Various somatostatin receptors (SSTR's) have been isolated, e.g., SSTR-1, SSTR-2, SSTR-3, SSTR-4, and SSTR-5. Thus, a somatostatin agonist may be one or more of an SSTR-1 agonist, SSTR-2 agonist, SSTR-3 agonist, SSTR-4 agonist or a SSTR-5 agonist. What is meant by a somatostatin type-2 receptor agonist (i.e., SSTR-2 agonist) is a compound which (1) has a high binding affinity (e.g., Ki of less than 100 nM or preferably less than 10 nm or less than 1 nM) for SSTR-2 (e.g., as defined by the receptor binding assay described below) and (2) decreases the rate of proliferation of medullary thyroid carcinoma cells (e.g., as shown by the biological assay described below). What is meant by a somatostatin type-2 receptor selective agonist is a somatostatin type-2 receptor agonist which has a higher binding affinity (i.e., lower Ki) for SSTR-2 than for SSTR-5. What is meant by a somatostatin type-5 receptor agonist is a somatostatin agonist which (1) has a high binding affinity (e.g., Ki of less than 100 nM or preferably less than 10 nm or less than 1 nM) for SSTR-5 (e.g., as defined by the receptor binding assay described below) and (2) attenuates the SSTR-2 agonist-induced decrease in the rate of proliferation of medullary thyroid carcinoma cells (e.g., as shown by the biological assay described below). What is meant by a somatostatin type-5 receptor selective agonist is a somatostatin type-5 receptor agonist which has a higher binding affinity (i.e., lower Ki) for SSTR-5 than for SSTR-2.

In one embodiment, the SSTR-2 agonist is also a SSTR-2 selective agonist. In another embodiment, the SSTR-2 selective agonist has a Ki value for SSTR-5 that is at least 2 times (e.g., at least 5 times or at least 10 times) higher than it has for the SSTR-2 receptor (e.g., as defined by the receptor binding assay described below).

Examples of SSTR-2 agonists which may be used to practice the present invention include, but are not limited to:

D-Nal-cyclo[Cys-Tyr-D-Trp-Lys-Val-Cys]-Thr-NH$_2$ (SEQ ID NO: 2), (Compound 1), cyclo[Tic-Tyr-D-Trp-Lys-Abu-Phe] (SEQ ID NO: 3), (Compound 2), 4-(2-Hydroxyethyl)-1-piperazinylacetyl-D-Phe-cyclo (Cys-Tyr-D-Trp-Lys-Abu-Cys)-Thr-NH$_2$ (SEQ ID NO: 4), (Compound 3), and 4-(2-Hydroxyethyl)-1-piperazine-2-ethanesulfonyl-D-Phe-cyclo(Cys-Tyr-D-Trp-Lys-Abu-Cys)-Thr-NH$_2$ (SEQ ID NO: 5), (Compound 4).

An example of SSTR-5 agonist which may be used to practice the present invention includes, but is not limited to:

D-Phe-Phe-Trp-D-Trp-Lys-Thr-Phe-Thr-NH$_2$ (SEQ ID NO: 1) (Compound 5).

Further examples of somatostatin agonists are those covered by formulae or those specifically recited in the publications set forth below, all of which are hereby incorporated by reference.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Note that for all somatostatin agonists described herein, each amino acid residue represents the structure of —NH—C(R)H—CO—, in which R is the side chain (e.g., CH$_3$ for Ala). Lines between amino acid residues represent peptide bonds which join the amino acids. Also, where the amino acid residue is optically active, it is the L-form configuration that is intended unless D-form is expressly designated. For clarity, disulfide bonds (e.g., disulfide bridge) which exist between two free thiols of Cys residues are not shown. Abbreviations of the common amino acids are in accordance with IUPAC-IUB recommendations.

Synthesis of Somatostatin Agonists

The methods for synthesizing somatostatin agonists is well documented and are within the ability of a person of ordinary skill in the art.

Synthesis of short amino acid sequences is well established in the peptide art. For example, synthesis of H-D-Phe-Phe-Phe-D-Trp-Lys-Thr-Phe-Thr-NH$_2$ (SEQ ID NO: 19) can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

Some of the compounds of the instant invention can have at least one asymmetric center. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The compounds of the instant invention generally can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The pharmaceutically acceptable salts can be formed by taking about 1 equivalent of a SSTR-2 agonist, e.g., compound 1, and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention includes within its scope pharmaceutical compositions comprising, as an active ingredient, at least one SSTR-2 agonist in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

MATERIALS AND METHODS

RT-PCR analysis was used to demonstrate that all five SSTR subtype mRNA's are expressed in a human MTC cell line, TT. The ability of SS analogues with differing affinity and specificity for SSTR2 and 5 subtypes to influence TT cell proliferative activity may be assessed by considering [$^3$H]thy incorporation, considered an indirect measure of DNA synthetic activity, and number of viable cells.

All SSTR2 preferential agonists were able to significantly suppress TT cell number at concentrations ranging from $10^{-9}$ M to $10^{-6}$ M. Compound 3 and Compound 4 significantly ($p<0.05$) reduced [$^3$H]thy incorporation at $10^{-9}$ M but not at $10^{-8}$ M and $10^{-7}$ M, when their maximal inhibitory effect on cell number was apparent. Each SSTR2 compound tested showed a trend for decreased efficacy with increasing concentration, however, bell-shaped response curves are common for SS. The inhibition of [$^3$H]thy incorporation and TT cell number by Compound 1 and Compound 2 at $10^{-7}$ M was not associated with any cytotoxic action, as demonstrated by Trypan Blue staining. Moreover, this effect was completely counteracted by cotreatment of TT cells with Compound 6, a selective SSTR2 antagonist. Taken together, these results indicate that SS analogues with preferential selectivity for SSTR2 inhibit TT cell proliferation by specifically interacting with SSTR2.

TT Cell Line Culture

The TT cell line was obtained from the American Type Culture Collection (ATCC, Manassas, Va., USA). The TT cell line consists of aneuploid transformed CT-producing parafollicular cells which are characterised by the presence of a TGC to TGG mutation (Cys to Trp) at exon 11 codon 634 in the RET protooncogene (Cooley L D, et al., 1995 Cancer Genet Cytogenet 80: 138-149), a characteristic that we confirmed in the cell line we worked with. Moreover, TT cells display an impaired expression of the tumor suppressor gene p53 (Velasco J A, et al., 1997 Int J Cancer 73: 449-455). Immunohistochemistry studies demonstrated that TT cells express CT and CT receptor (Frendo J L, et al., 1994 FEBS Lett. 342: 214-216), carcino-embrionic antigen (CEA), SS, neurotensin, gastrin-releasing peptide (GRP), Leu- and Met-enkephalin, parathyroid hormone releasing peptide (PTHrp), Chromogranin A, SP-I, Synaptophysin, Neuron-specific enolase (NSE), 1,25-dihydroxyvitamin $D_3$ receptor, Thyrosin hydroxylase, α-Tubulin, and Cytocheratin (Zabel M, et al., 1995 Histochemical J. 27: 859-868). TT cells secrete a significant amount of CT and respond to changes in ionised calcium levels (Zabel M, et al., 1992 Histochemistry 102: 323-327). Thus the TT cell line is suitable for studies on parafollicular function and responses to endocrine and pharmacological stimuli.

Cells were maintained in Ham's Nutrient Mixture F12 with Glutamine (EuroClone Ltd, Torquay, UK), supplemented with 10% fetal bovine serum (FBS, Life Technologies, Milano, Italy), 100 U/mL penicillin, 0.1 mg/mL streptomycin, and 100 µg/mL amphotericin (EuroClone Ltd, Torquay, UK) at 37° C. in a humidified atmosphere of 5% $CO_2$ and 95% air.

Isolation of RNA

Total RNA was extracted from subconfluent TT cells by using TRIZOL (Life Technologies, Milano, Italy). The TRIZOL protocol is a modification of the guanidinium/phenol extraction. Briefly, the cultured cell media was aspirated and the cells washed with 1×PBS. The TRIZOL reagent was added and cells lysed at room temperature for 10 min. Chloroform was added to the TRIZOL/cell lysate mixture, and left to stand for 2-3 min, and then centrifuged 12000×g for 15 min. The aqueous layer was removed from the centrifuged mixture. Isopropanol was added to precipitate the RNA, the pellet collected, washed with 75% ethanol and dried in air. Total RNA was resuspended in diethylpyrocarbonate-treated (DEPC) water and quantified using UV spectrophotometry at 260 nM. To prevent DNA contamination, RNA was treated with ribonuclease-free deoxyribonuclease (Promega, Milano, Italy).

RT-PCR

Using a first strand complementary DNA (cDNA) synthesis kit (SuperScript Preamplification System for First Strand cDNA Synthesis, Life Technologies, Milano, Italy), 1 µg total RNA was reverse transcribed according to the manufacturer's protocol. RT mix in PCR tubes was covered with 50 µl light white mineral oil (Sigma-Aldrich Corp. Milano, Italy); the RT was carried out in the Minicycler (MJ Research Inc., Watertown, Mass., USA) using a program with the following parameters: 10 min at 70° C., 1 min at 4° C., 5 min at 4° C. After supplementing with SuperScript II, the reaction was completed at 42° C. for 50 min then at 70° for 15 min. Samples were digested with RNAse H (Promega, Milano, Italy) at 37° C. for 20 min, and then stored at −20° C. until the first PCR.

The cDNA (1 µl of RT reaction) was then amplified by PCR with 1 U Taq DNA polymerase (Life Technologies, Milano, Italy), in the conditions recommended by suppliers in a 50-µl reaction mixture. After initial denaturation at 95° C. for 5 min, PCR reactions were carried out using the oligonucleotide primers and the conditions listed in Table 1, describing the size of expected fragments. PCR products were analyzed on a 2% agarose gel and visualized by ethidium bromide (ETB) staining. To assure that no contamination occurred during the course of the RT-PCR procedure, two kinds of negative control were prepared. The first negative control was made by omitting the total RNA in the RT. The second was prepared by replacing the cDNA mix with water in the PCR reaction. The PCR was considered useful only if no band was observed in the negative control lanes on a 2% agarose gel. Each PCR product was subjected to restriction enzyme digestion and analysed on 2% agarose gel to further confirm the correct identification of the amplicons.

SSTR Selective Agonists and Antagonists

SS analogues used in this study and their respective affinities to the different SSTR's are listed in Table 2. Each compound, provided by Biomeasure Incorporated (Milford, Mass., USA), was resuspended in 0.01 N acetic acid containing 0.1% bovine serum albumin (BSA) in order to provide uniform solubility and prevent non-specific binding to the various preparation surfaces. Specificity and selectivity of the analogues were determined by Radioligand Binding Assay on CHO-K1 cells stably transfected with each of the SSTR subtypes, as follows.

The complete coding sequences of genomic fragments of the SSTR 1, 2, 3, and 4 genes and a cDNA clone for SSTR 5 were subcloned into the mammalian expression vector pCMV (Life Technologies, Milano, Italy). Clonal cell lines stably expressing SSTR's 1-5 were obtained by transfection into CHO-K1 cells (ATCC, Manassas, Va., USA) using the calcium phosphate co-precipitation method (Davis L, et al., 1994 In: Basic methods in Molecular Biology, 2nd edition, Appleton & Lange, Norwalk, Conn., USA: 611-646). The plasmid pRSV-neo (ATCC) was included as a selectable marker. Clonal cell lines were selected in RPMI 1640 media containing 0.5 mg/ml of G418 (Life Technologies, Milano, Italy), ring cloned, and expanded into culture.

Membranes for in vitro receptor binding assays were obtained by homogenizing the CHO-K1 cells expressing the SSTR's subtypes in ice-cold 50 mM Tris-HCl and centrifuging twice at 39000 g (10 min), with an intermediate resuspension in fresh buffer. The final pellets were resuspended in 10 mM Tris-HCl for assay. For the SSTR 1, 3, 4, and 5 assays, aliquots of the membrane preparations were incubated 90 min. at 25° C. with 0.05 nM [$^{125}$I-Tyr11]SS-14 in 50 mM HEPES (pH 7.4) containing 10 mg/ml BSA, 5 mM $MgCl_2$, 200 KIU/ml Trasylol, 0.02 mg/ml bacitracin, and 0.02 mg/ml phenylmethylsuphonyl fluoride. The final assay volume was 0.3 ml. For the SSTR 2 assay, 0.05 nM [$^{125}$I]MK-678 was employed as the radioligand and the incubation time was 90 min at 25° C. The incubations were terminated by rapid filtration through GF/C filters (pre-soaked in 0.3% polyethylenimine) using a Brandel filtration manifold. Each tube and filter were then washed three times with 5 ml aliquots of ice-cold buffer. Specific binding was defined as the total radioligand bound minus that bound in the presence of 1000 nM SS-14 for SSTR 1, 3, 4, and 5, or 1000 nM MK-678 for SSTR2.

Biological Activity Evaluation

Figure 1:
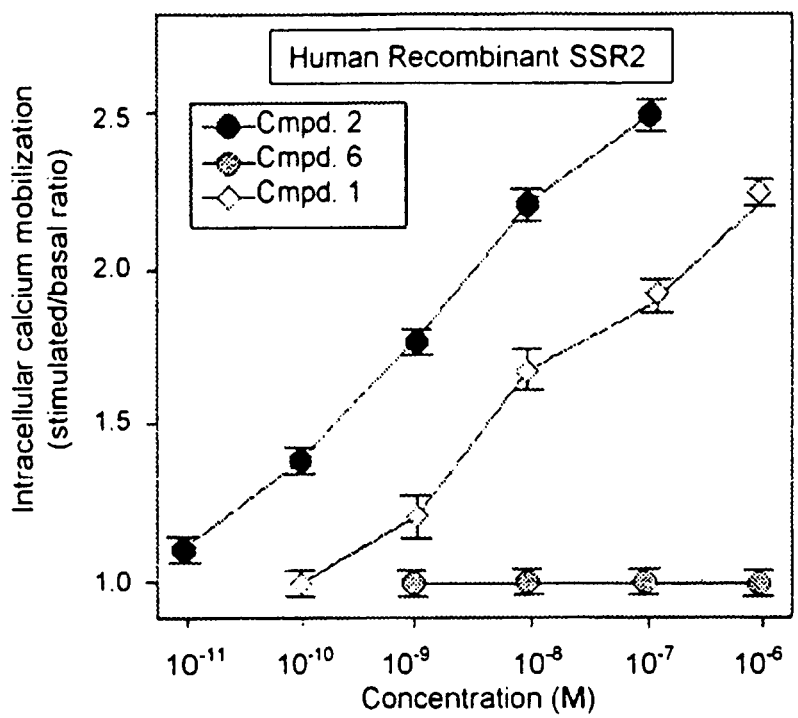
FIG. 1: In Vitro SSTR2 Mediated Intracellular Calcium Mobilization

Biological activity of SSTR selective agonists and antagonists was evaluated by the calcium mobilization assay in CHO-K1 cells expressing the human SSTR2 or SSTR5. The cells were harvested by incubating in a 0.3% EDTA/phosphate buffered saline solution (25° C.), and washed twice by centrifugation. The washed cells were resuspended in Hank's—buffered saline solution (HBSS) for loading of the fluorescent $Ca^{2+}$ indicator Fura-2AM. Cell suspensions (approximately $10^6$ cells/ml) were incubated with 2 mM Fura-2AM for 30 min at 25° C. Unloaded Fura-2AM was removed by centrifugation twice in HBBS, and the final suspensions were transferred to a spectrofluorometer (Hitachi F-2000) equipped with a magnetic stirring mechanism and a temperature-regulated cuvette holder. After equilibration to 37° C., the SS analogues were added for measurement of intracellular $Ca^{2+}$ mobilization. The excitation and emission wavelengths were 340 and 510 nm, respectively. In the SSTR2 expressing cells (FIG. 1), Compound 2 and Compound 1 stimulated significant intracellular $Ca^{2+}$ mobilization (indicated as the ratio between stimulated and basal value), whereas Compound 6 did not, at the concentrations tested. In addition, Compound 4 and Compound 3 were also highly potent in stimulating $Ca^{2+}$ mobilization. In the SSTR5 expressing cells (FIG. 2), Compound 5 and Compound 1 stimulated significant intracellular $Ca^{2+}$ mobilization, whereas Compound 6 displayed slight agonist activity in the range of 300 to 1000 nM. In the SSTR2 expressing cells (FIG. 3), Compound 6 inhibited SS-induced intracellular $Ca^{2+}$ mobilization in SSTR2 expressing cells in a dose dependent manner with complete suppression of SS action at about $10^{-7}$ M. Therefore the evaluation of intracellular $Ca^{2+}$ mobilization demonstrated that the biological activity of each of the various analogues was in keeping with its receptor binding profile.

DNA Synthesis

The effects of SSTR selective agonists and antagonists on TT cell DNA synthesis were assessed by determining the rate of [$^3$H]thymidine ([$^3$H]thy) incorporation, as previously described (Davis L, et al., 1994 In: Basic methods in Molecular Biology, 2nd edition, Appleton & Lange, Norwalk, Conn., USA: 611-646, degli Uberti E C, et al., 1991 J Clin Endocrinol Metab 72: 1364-1371). TT cells were plated in 24-multiwell plates ($10^5$ cells/well) and incubated for 48 hours in a medium supplemented with 10% FBS in the presence of [$^3$H]thy (1.5 µCi/mL; 87 Ci/mmol) with or without each SS analogue at concentrations ranging from $10^{-6}$ to $10^{-9}$ M. Treatments were renewed by adding fresh analogues to the wells after the first 24 h of incubation, without removing the medium.

After incubation, the cells were washed three times with ice-cold PBS and twice with 10% ice-cold trichloroacetic acid (TCA). TCA-precipitated material was solubilized in 500 µL 0.2 mol/L sodium hydroxide and 0.1% SDS. Cell-associated radioactivity was then counted in a scintillation spectrometer. Results (counts per min per well) were obtained by determining the mean value of at least six experiments in quadruplicate. The viability of TT cells in control and treated cultures was evaluated by Trypan blue staining both after 24 and 48 hours, and the number of viable cells was always 85-95%.

Cell Proliferation

The effects of SSTR selective agonists and antagonists on TT cell proliferation were assessed by the CELLTITER 96 Aqueous Non-Radioactive Cell Proliferation Assay (Promega, Milano, Italy), a calorimetric method for determining the number of viable cells in proliferation assays. The assay contains solutions of a tetrazolium compound (Owen's reagent; MTS) and an electron coupling reagent (phenazine methosulphate; PMS). MTS is bioreduced by cells into a formazan that is soluble in tissue culture medium. The absorbance of the formazan at 490 nm can be measured directly from 96 well assay plates (Zatelli M C, et al., 2000 J Clin Endocrinol Metab 85: 847-852; Cory A H, et al., 1991 Cancer Commun 3: 207-212). The conversion of MTS into the aqueous soluble formazan is accomplished by dehydrogenase enzymes found in metabolically active cells. The quantity of formazan product as measured by the amount of 490 nm absorbance is directly proportional to the number of living cells in culture. Briefly, TT cells were plated in 96-multiwell plates ($2 \times 10^4$ cells/well) and incubated for 48 hours in a medium supplemented with 10% FBS in the presence or absence of each SS analogue at concentrations ranging from $10^{-6}$ to $10^{-9}$ M. Treatments were renewed by adding fresh analogues to the wells after the first 24 hours of incubation. At the end of the incubation period, 20 µl of a combined MTS/PMS solution were added to each well with a repeating pipette, and the plates were incubated for an additional 4 hours at 37° C. in a humidified 5% $CO_2$ atmosphere. The absorbance at 490 nm was then recorded using an ELISA plate reader (EASIA Reader, Medgenix, Camarillo, Calif.). Results (absorbance at 490 nm) were obtained by determining the mean value of at least six experiments in eight replicates.

Results

SSTR Expression in the Human MTC Cell Line TT

To understand the individual role of SSTR2 and SSTR5 subtypes in controlling parafollicular C cell proliferation, we evaluated whether TT cells express SSTR's that could mediate a potential response to selective compounds for individual SSTR subtypes. To address this question, we isolated total RNA from cultured TT cells and performed RT-PCR reactions in the conditions described in Material and Methods. Integrity of cDNA was assured by the presence of the GAPDH signal. The absence of genomic DNA contamination in the cDNA samples was assessed by the lack of any amplification in a PCR reaction using non-reverse transcribed samples. Positive amplification of SSTR1, 2, 3, 4, and 5 was found in the examined cell line (FIG. 4), demonstrating that these receptors are expressed in human MTC cell-line TT. The demonstration that the TT cell line stably expresses SSTR subtypes made this cellular model system suitable for evaluating the action of receptor-selective SS analogues.

Effect of Selective SS Analogues on TT Cell [$^3$H]thy Incorporation

[$^3$H]Thy incorporation values obtained with $10^{-9}$ to $10^{-6}$ M concentrations of SSTR2 preferential agonists (Compound 1, Compound 2, Compound 3, and Compound 4), SSTR5 preferential agonist (Compound 5) and SSTR2 preferential antagonist (Compound 6) are presented in FIG. 5. As indicated, Compound 2 significantly suppressed [$^3$H]thy incorporation by 58-23% at concentrations ranging from $10^{-9}$ to $10^{-7}$ M. Compound 1 significantly suppressed [$^3$H]thy incorporation by 41-21% at concentrations ranging from $10^{-9}$ to $10^{-6}$ M. [$^3$H]thy incorporation was also significantly reduced by Compound 4 (−13%, p<0.05) and Compound 3 (−17%, p<0.05) at $10^{-9}$ M. In contrast, Compound 5 significantly increased [$^3$H]thy incorporation in TT cells by 80-175%. The SSTR2 selective antagonist, Compound 6, did not alter TT cell [$^3$H]thy incorporation compared with untreated control cells.

Effect of Selective SS Analogues on TT Cell Proliferation

To examine in more detail the activity of SS-analogues on TT cell growth, their effect on viable cell number was also analyzed. The effects of SSTR2 preferential agonists, an SSTR5 preferential agonist and an SSTR2 preferential antagonist on viable TT cell number at concentrations ranging from $10^{-9}$ to $10^{-6}$ M are represented in FIG. 6. As indicated, all SSTR2 preferential compounds significantly inhibited cell proliferation when compared with untreated control cells at each concentration tested. The selective SSTR5 agonist, Compound 5, produced a slight increase of TT cell proliferation (up to 11% at $10^{-8}$ M), however this did not represent a statistical difference from the untreated control cells. The selective SSTR2 antagonist, Compound 6, did not appear to affect TT cell growth at the concentrations tested.

Selective SSTR2 Antagonist Counteracts the Effects of SSTR2-Preferential Agonist To further clarify whether SSTR2 is specifically involved in mediating the antiproliferative activity of SSTR2 preferential agonists, [$^3$H]thy incorporation and cell growth were evaluated in TT cells exposed for 48 hours to Compound 1 and Compound 2, each either alone (at $10^{-7}$ M) or in combination with Compound 6, a selective SSTR2 antagonist at equimolar concentration ($10^{-7}$ M). The inhibition of [$^3$H]thy incorporation induced by both Compound 1 and Compound 2 was suppressed by cotreatment of TT cells with Compound 6 (FIG. 7, upper panel). TT cell proliferation inhibition induced by Compound 1 was significantly reduced from 46% to 10% by cotreatment with Compound 6. Further, Compound 6 appeared to block completely the antiproliferative activity of Compound 2 (FIG. 7, lower panel). Thus, the specific involvement of SSTR2 in mediating the inhibitory effect of an SSTR2 agonist on TT cell proliferation is clearly demonstrated.

Effect of Combination of a Preferential SSTR2 Agonist with a Preferential SSTR5 Agonist on [$^3$H]thy Incorporation and Cell Proliferation In order to analyze the effects of an SSTR2 and an SSTR5 agonist in combination, TT cell [$^3$H]thy incorporation and proliferation were examined testing each of Compound 2 and Compound 5 at $10^{-7}$ M in combination with increasing doses (from $10^{-9}$ M to $10^{-6}$ M) of the other compound. The results are summarized in FIG. 8. Increasing concentrations of the SSTR5 agonist ($10^{-9}$ M to $10^{-6}$ M) dose-dependently prevented the suppression of TT cell [$^3$H]thy incorporation (FIG. 8, upper panel) and proliferation (FIG. 8, lower panel) produced by the SSTR2 agonist ($10^{-7}$ M). These data demonstrate an antagonism between SSTR5 and SSTR2 mediated effects on proliferation.

It is to be understood that while the invention has been described in conjunction with the detailed description thereof, that the foregoing description is intended to illustrate and not limit the scope of the invention defined by the appended claims. Other aspects, advantages, and modifications are within the claims.

TABLE 1

Primers and PCR conditions for SSRs amplification

| SSR | Primers | Denaturation | Annealing | Extension | Cycles | Expected fragment (bp) |
|---|---|---|---|---|---|---|
| 1 | For: 5'-AGCCGGTTGACTATTACGCC-3' (SEQ ID NO: 7)<br>Rev: 5'-GCTCTCACTTCTACCATTGTC-3' (SEQ ID NO: 8) | 95° C., 30" | 60° C., 1' | 72° C., 2' | 45 | 334 |
| 2 | For: 5'-GGTGAA GTCCTCTGGAATCC-3' (SEQ ID NO: 9)<br>Rev: 5'-CCATTGCCAGTAGACAGAGC-3' (SEQ ID NO: 10) | 95° C., 30" | 63° C., 1' | 72° C., 2' | 45 | 461 |
| 3 | For: 5'-TCATCTGCCTCTGCTACCTG-3' (SEQ ID NO: 11)<br>Rev: 5'-GAGCCCAAAGAAGGCAGGCT-3' (SEQ ID NO: 12) | 95° C., 30" | 65° C., 1' | 72° C., 2' | 45 | 221 |
| 4 | For: 5'-CGGCAGTCTTCGTGGTCTAC-3' (SEQ ID NO: 13)<br>Rev: 5'-GCATCAAGGTCGGTCACGAC-3' (SEQ ID NO: 14) | 94° C., 30" | 63° C., 1' | 72° C., 2' | 45 | 247 |
| 5 | For: 5'-AACACGCTGGTCATCTACGTGGT-3' (SEQ ID NO: 15)<br>Rev: 5'-AGACACTGGTGAACTGGTTGAC-3' (SEQ ID NO: 16) | 94° C., 1' | 60° C., 1' | 72° C., 1' 15" | 40 | 211 |
| GAPDH | For: 5'-ATGACCCCTTCATTGACCTC-3' (SEQ ID NO: 17)<br>Rev: 5'-AAGTGGTCGTTGAGGGCAAT-3' (SEQ ID NO: 18) | 95° C., 30" | 60° C., 1' | 72° C., 2' | 40 | 820 |

TABLE 2

Human somatostatin receptor subtype specificity (Ki, nM)

| Compound | Receptor Subtype | | | | |
|---|---|---|---|---|---|
| | 1 | 2 | 3 | 4 | 5 |
| 1 | 2129 | 0.75 | 98 | 1826 | 12.7 |
| 2 | 1000 | 0.34 | 412 | 1000 | 213.5 |
| 3 | 5210 | 0.35 | 215 | 7537 | 11.2 |
| 4 | 6016 | 0.19 | 26.8 | 3897 | 9.8 |
| 5 | 1152 | 166 | 1000 | 1618 | 2.4 |
| 6 (antagonist) | 2757 | 6.4 | 44 | 423 | 86.5 |

Subtype affinity was determined by radioligand membrane receptor binding assays in Chinese hamster ovary cells expressing human SSR2 gene or SSR5 cDNA

What is claimed is:

1. A somatostatin type-2 receptor antagonist comprising the formula Cpa-cyclo(D-Cys-4-Pal-D-Trp-Lys-Thr-Cys)-Nal-NH$_2$ (SEQ ID NO: 6) or a pharmaceutically acceptable salt thereof.

* * * * *